(12) United States Patent
Tanaka

(10) Patent No.: US 10,561,388 B2
(45) Date of Patent: Feb. 18, 2020

(54) RADIOGRAPHING SYSTEM, MOBILE TERMINAL, RADIOGRAPHING APPARATUS, RADIOGRAPHING METHOD, AND STORAGE MEDIUM

(71) Applicant: CANON KABUSHIKI KAISHA, Tokyo (JP)

(72) Inventor: Ryo Tanaka, Tokyo (JP)

(73) Assignee: Canon Kabushiki Kaisha, Tokyo (JP)

(\*) Notice: Subject to any disclaimer, the term of this patent is extended or adjusted under 35 U.S.C. 154(b) by 227 days.

(21) Appl. No.: 15/473,422

(22) Filed: Mar. 29, 2017

(65) Prior Publication Data

US 2017/0281113 A1 Oct. 5, 2017

(30) Foreign Application Priority Data

Apr. 1, 2016 (JP) .................................. 2016-074473

(51) Int. Cl.
*A61B 6/00* (2006.01)

(52) U.S. Cl.
CPC .............. *A61B 6/5211* (2013.01); *A61B 6/40* (2013.01); *A61B 6/42* (2013.01); *A61B 6/4208* (2013.01); *A61B 6/4283* (2013.01); *A61B 6/4411* (2013.01); *A61B 6/4452* (2013.01); *A61B 6/461* (2013.01); *A61B 6/52* (2013.01); *A61B 6/5205* (2013.01); *A61B 6/54* (2013.01); *A61B 6/544* (2013.01); *A61B 6/545* (2013.01); *A61B 6/548* (2013.01); *A61B 6/563* (2013.01)

(58) Field of Classification Search
CPC ....... A61B 6/42; A61B 6/4208; A61B 6/4266; A61B 6/44; A61B 6/4405; A61B 6/4411; A61B 6/4452; A61B 6/5211; A61B 6/5294; A61B 6/56; A61B 6/563; A61B 6/566; A61B 6/4283; A61B 6/52; A61B 6/5205; A61B 6/40; A61B 6/46; A61B 6/461; A61B 6/54; A61B 6/542; A61B 6/544; A61B 6/545; A61B 6/548
USPC ....................................................... 378/62, 91
See application file for complete search history.

(56) References Cited

U.S. PATENT DOCUMENTS

| | | | | |
|---|---|---|---|---|
| 6,859,513 | B2* | 2/2005 | Sako | A61B 6/00 378/16 |
| 7,092,970 | B2* | 8/2006 | Shiibashi | G06Q 10/10 |
| 7,428,294 | B2* | 9/2008 | Spahn | A61B 6/541 250/370.09 |
| 7,476,834 | B2* | 1/2009 | Umeki | A61B 8/4416 250/208.1 |

(Continued)

FOREIGN PATENT DOCUMENTS

| | | |
|---|---|---|
| JP | 3494683 B2 | 2/2004 |
| JP | 2005-111054 A | 4/2005 |
| JP | 2009-89723 A | 4/2009 |

*Primary Examiner* — Allen C. Ho
(74) *Attorney, Agent, or Firm* — Canon U.S.A. Inc., IP Division

(57) ABSTRACT

A radiographing system includes a mobile terminal configured to store an examination time of a subject that is based on examination-related information about the subject, a radiographing apparatus configured to take a radiation image of the subject based on the examination-related information and to store an imaging time of the radiation image, and an association unit configured to associate the radiation image with the examination-related information based on the imaging time and the examination time.

16 Claims, 14 Drawing Sheets

(56) References Cited

U.S. PATENT DOCUMENTS

| | | | | |
|---|---|---|---|---|
| 7,545,914 | B2* | 6/2009 | Kito | A61B 6/4283 378/207 |
| 7,664,842 | B2* | 2/2010 | Tanaka | A61B 6/4405 709/200 |
| 7,751,529 | B2* | 7/2010 | Ohara | A61B 6/00 378/116 |
| 7,764,765 | B2* | 7/2010 | Ohta | A61B 6/4233 250/370.09 |
| 7,767,981 | B2* | 8/2010 | Kuwabara | A61B 6/4216 250/484.4 |
| 8,021,045 | B2* | 9/2011 | Foos | A61B 6/4405 378/198 |
| 8,107,590 | B2* | 1/2012 | Nishino | A61B 6/00 250/370.09 |
| 8,204,286 | B2* | 6/2012 | Sendai | A61B 6/4405 378/117 |
| 8,280,129 | B2* | 10/2012 | Futami | G16H 10/60 382/128 |
| 8,295,439 | B2* | 10/2012 | Yonekawa | A61B 6/00 378/115 |
| 8,393,789 | B2* | 3/2013 | Enomoto | A61B 6/00 378/207 |
| 8,494,247 | B2* | 7/2013 | Watanabe | A61B 6/00 378/115 |
| 8,550,709 | B2* | 10/2013 | Nishino | A61B 6/04 378/145 |
| 8,704,188 | B2* | 4/2014 | Kitano | A61B 6/548 250/370.09 |
| 8,705,700 | B2* | 4/2014 | Eguchi | A61B 6/4233 378/116 |
| 8,729,484 | B2* | 5/2014 | Nishino | G01T 1/2018 250/370.09 |
| 8,744,156 | B2* | 6/2014 | Abe | G06F 19/321 382/131 |
| 8,781,073 | B2* | 7/2014 | Kim | A61B 6/46 378/98 |
| 8,798,235 | B2* | 8/2014 | Ohta | A61B 6/4494 250/370.09 |
| 8,841,628 | B2* | 9/2014 | Kitano | H01L 27/14663 250/393 |
| 8,917,928 | B2* | 12/2014 | Koishi | G06T 7/0014 382/132 |
| 8,929,510 | B2* | 1/2015 | Nishino | A61B 6/4216 378/102 |
| 8,942,444 | B2* | 1/2015 | Liu | A61B 6/563 382/128 |
| 9,020,097 | B2* | 4/2015 | Iwakiri | A61B 6/4283 378/42 |
| 9,044,191 | B2* | 6/2015 | Nishino | A61B 6/4405 |
| 9,088,893 | B2* | 7/2015 | Sugahara | H04W 12/06 |
| 9,125,611 | B2* | 9/2015 | Eaves | A61B 6/4405 |
| 9,131,593 | B2* | 9/2015 | Arima | H05G 1/30 |
| 9,131,905 | B2* | 9/2015 | Abe | A61B 6/00 |
| 9,168,016 | B2* | 10/2015 | Ohta | G01T 1/24 |
| 9,258,464 | B2* | 2/2016 | Ohta | H04N 5/321 |
| 9,313,868 | B2* | 4/2016 | Arima | H05G 1/30 |
| 9,326,745 | B2* | 5/2016 | Muraoka | A61B 6/4233 |
| 9,357,974 | B2* | 6/2016 | Foos | A61B 6/4405 |
| 9,402,592 | B2* | 8/2016 | Garcia | A61B 6/4283 |
| 9,405,183 | B2* | 8/2016 | Ando | A61B 6/4266 |
| 9,492,137 | B2* | 11/2016 | Iwamoto | A61B 6/4283 |
| 9,514,529 | B2* | 12/2016 | Takagi | A61B 6/563 |
| 9,521,987 | B2* | 12/2016 | Tajima | A61B 6/08 |
| 9,532,756 | B2* | 1/2017 | Wakai | A61B 5/00 |
| 9,538,978 | B2* | 1/2017 | Makino | G16H 40/63 |
| 9,615,810 | B2* | 4/2017 | Matsuno | A61B 6/00 |
| 9,642,589 | B2* | 5/2017 | Profio | A61B 6/545 |
| 9,649,074 | B2* | 5/2017 | Simon | A61B 6/025 |
| 9,655,575 | B2* | 5/2017 | Park | A61B 6/4233 |
| 9,661,729 | B2* | 5/2017 | Arima | A61B 6/461 |
| 9,662,086 | B2* | 5/2017 | Ohta | A61B 5/0059 |
| 9,665,254 | B2* | 5/2017 | Hayashi | A61B 6/463 |
| 9,681,850 | B2* | 6/2017 | Park | A61B 6/542 |
| 9,700,278 | B2* | 7/2017 | Tezuka | A61B 6/563 |
| 9,730,658 | B2* | 8/2017 | Tajima | H04N 5/32 |
| 9,757,086 | B2* | 9/2017 | Tezuka | A61B 6/54 |
| 9,814,435 | B2* | 11/2017 | Kim | A61B 6/469 |
| 9,855,018 | B2* | 1/2018 | Hamano | A61B 6/4233 |
| 9,861,334 | B2* | 1/2018 | Tajima | A61B 6/5294 |
| 9,880,111 | B2* | 1/2018 | Oda | H04N 5/32 |
| 9,892,521 | B2* | 2/2018 | Enomoto | A61B 6/4233 |
| 9,904,767 | B2* | 2/2018 | Desai | A61B 6/548 |
| 9,931,092 | B2* | 4/2018 | Tajima | A61B 6/488 |
| 9,980,696 | B2* | 5/2018 | Oda | A61B 6/465 |
| 10,016,173 | B2* | 7/2018 | Foos | A61B 6/03 |
| 10,022,102 | B2* | 7/2018 | Okada | A61B 6/542 |
| 10,022,105 | B2* | 7/2018 | Kudo | G08B 29/185 |
| 10,039,509 | B2* | 8/2018 | Okusu | G06F 3/04845 |
| 10,098,598 | B2* | 10/2018 | Lee | A61B 6/465 |
| 10,126,925 | B2* | 11/2018 | Arima | A61B 6/00 |
| 10,172,578 | B2* | 1/2019 | Lee | A61B 6/4417 |
| 10,172,583 | B2* | 1/2019 | Enomoto | A61B 6/4241 |
| 10,188,365 | B2* | 1/2019 | Lee | A61B 6/40 |
| 10,349,913 | B2* | 7/2019 | Enomoto | A61B 6/5282 |
| 10,349,915 | B2* | 7/2019 | Xu | G16H 30/20 |
| 10,368,826 | B2* | 8/2019 | Tamura | A61B 6/4283 |
| 10,398,400 | B2* | 9/2019 | Kim | A61B 6/4291 |
| 10,433,809 | B2* | 10/2019 | Park | H04W 76/10 |
| 2016/0157810 | A1 | 6/2016 | Tezuka | |

* cited by examiner

FIG.7

701 — PATIENT NAME:

PATIENT ID:

EXAMINATION ID:

EXAMINATION DATE AND TIME:

CANCEL

702
EXAMINATION ACQUISITION

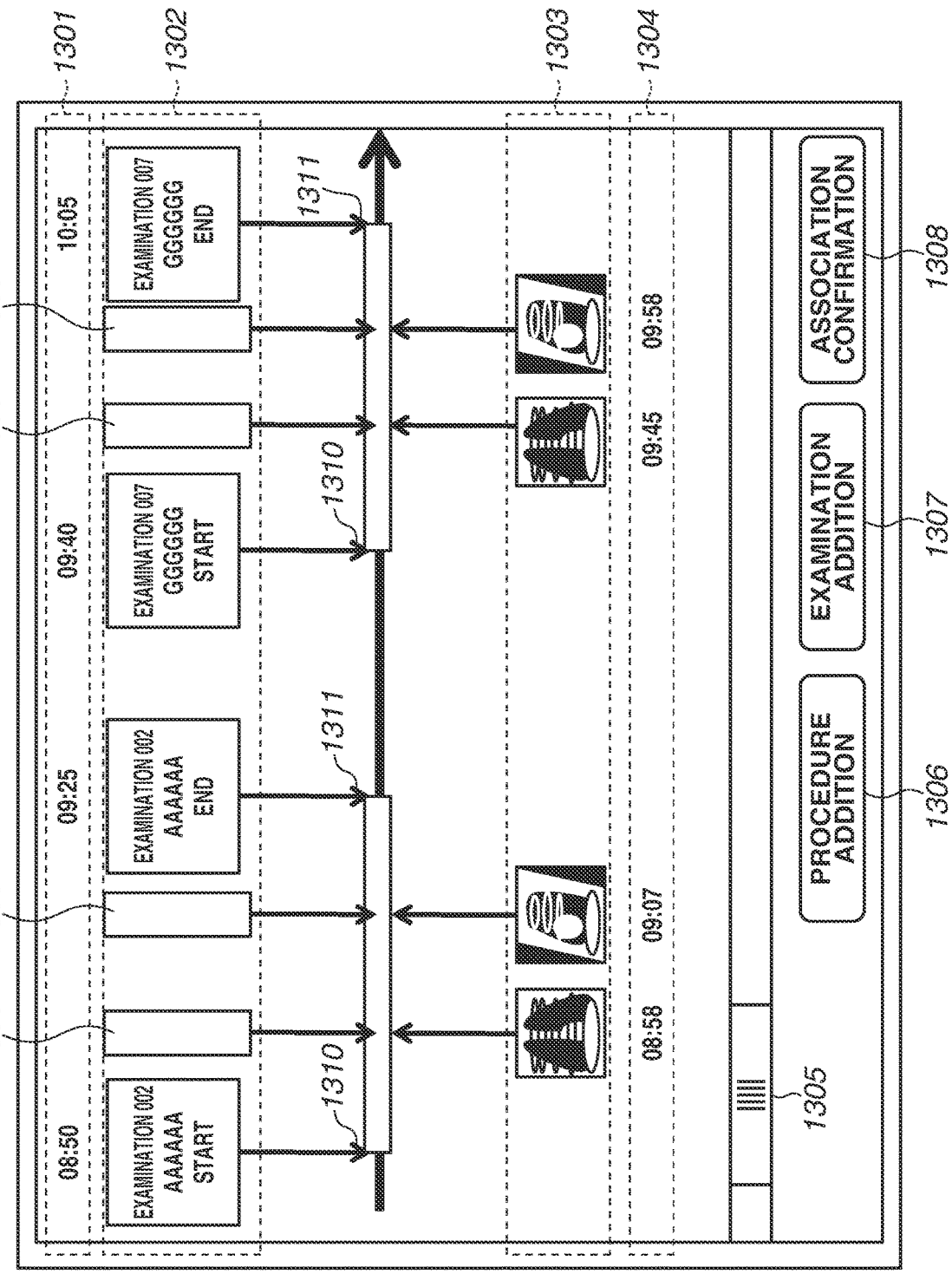

FIG. 14

1401
- PATIENT NAME:
- DATE OF BIRTH:      AGE:
- PATIENT ID:
- GENDER: ○ MALE  ○ FEMALE  ○ OTHERS

1402 — LIST OF RADIOGRAPHIC PROCEDURES

| FRONT BONE OF SKULL | LATERAL BONE OF SKULL | LATERAL BONE OF SKULL |
| --- | --- | --- |
| FRONT CERVICAL VERTEBRA | LATERAL CERVICAL VERTEBRA | LATERAL CERVICAL VERTEBRA |
| FRONT CHEST | LATERAL CHEST | LATERAL CHEST |
| FRONT THORACIC VERTEBRA | LATERAL THORACIC VERTEBRA | LATERAL THORACIC VERTEBRA |
| FRONT ABDOMINAL | LATERAL ABDOMINAL | LATERAL ABDOMINAL |
| FRONT ABDOMINAL | LATERAL ABDOMINAL | LATERAL ABDOMINAL |

1403 — SELECTED RADIOGRAPHIC PROCEDURE
- FRONT CHEST
- LATERAL CHEST

1404 — EXAMINATION ADDITION

RADIOGRAPHING SYSTEM, MOBILE TERMINAL, RADIOGRAPHING APPARATUS, RADIOGRAPHING METHOD, AND STORAGE MEDIUM

BACKGROUND OF THE INVENTION

Field of the Invention

Aspects of the present disclosure generally relate to a radiographing system, a mobile terminal, a radiographing apparatus, a radiographing method, and a storage medium, which are configured to associate a radiation image with examination-related information about a subject.

Description of the Related Art

Currently, a radiation image which is obtained by imaging the intensity of radiation passing through a subject is usually formed as a digital image. For example, in the case of a computed radiography (CR) apparatus, radiation is accumulated in an imaging plate (IP), which is contained in a cassette. Then, a reading device irradiates the IP with laser light and, at the same time, scans the amount of light emitted from the IP, thus obtaining a digital image.

The CR apparatus is configured with the cassette, the reading device, and a control device. The reading device reads individual discrimination information and a radiation image from the cassette, and transmits those to the control device. The control device associates the radiation image with an examination order stored in the control device based on the individual discrimination information read from the cassette.

In recent years, a flat panel detector (FPD), which detects and converts radiation into a digital image without the need for a reading device, has been widely used. The FPD contains a storage region therein and is thus capable of storing a plurality of digital X-ray images (Japanese Patent No. 3,494,683).

However, allowing a plurality of images to be stored in one FPD makes it difficult to associate the radiation image with the examination order based on the individual discrimination information as in the above-mentioned CR apparatus. In the case of a method for associating a radiation image with an examination order discussed in Japanese Patent Application Laid-Open No. 2009-89723, it is necessary to input individual discrimination information about an FPD to an examination recording device at the time of every radiographing operation.

SUMMARY OF THE INVENTION

Aspects of the present disclosure are generally directed to making radiography more efficient while decreasing the risk for patient mix-up and any other misunderstandings.

According to an aspect of the present disclosure, a radiographing system includes a mobile terminal configured to store an examination time of a subject that is based on examination-related information about the subject, a radiographing apparatus configured to take a radiation image of the subject based on the examination-related information and to store an imaging time of the radiation image, and an association unit configured to associate the radiation image with the examination-related information based on the imaging time and the examination time.

Further features of the present disclosure will become apparent from the following description of exemplary embodiments with reference to the attached drawings.

BRIEF DESCRIPTION OF THE DRAWINGS

FIG. 7 illustrates an example of a search screen, which is displayed by a display unit.

FIG. 13 illustrates an example of an association result screen, which is displayed by the display unit.

FIG. 14 illustrates an example of an examination addition screen, which is displayed by the display unit.

DESCRIPTION OF THE EMBODIMENTS

Various exemplary embodiments, features, and aspects of the disclosure will be described in detail below with reference to the drawings. Furthermore, while the following exemplary embodiments are described based on, for example, a case where X-rays are applied as radiation, radiation is not limited to X-rays, but can be, for example, electromagnetic waves, alpha rays, beta rays, and gamma rays.

Figure 1:
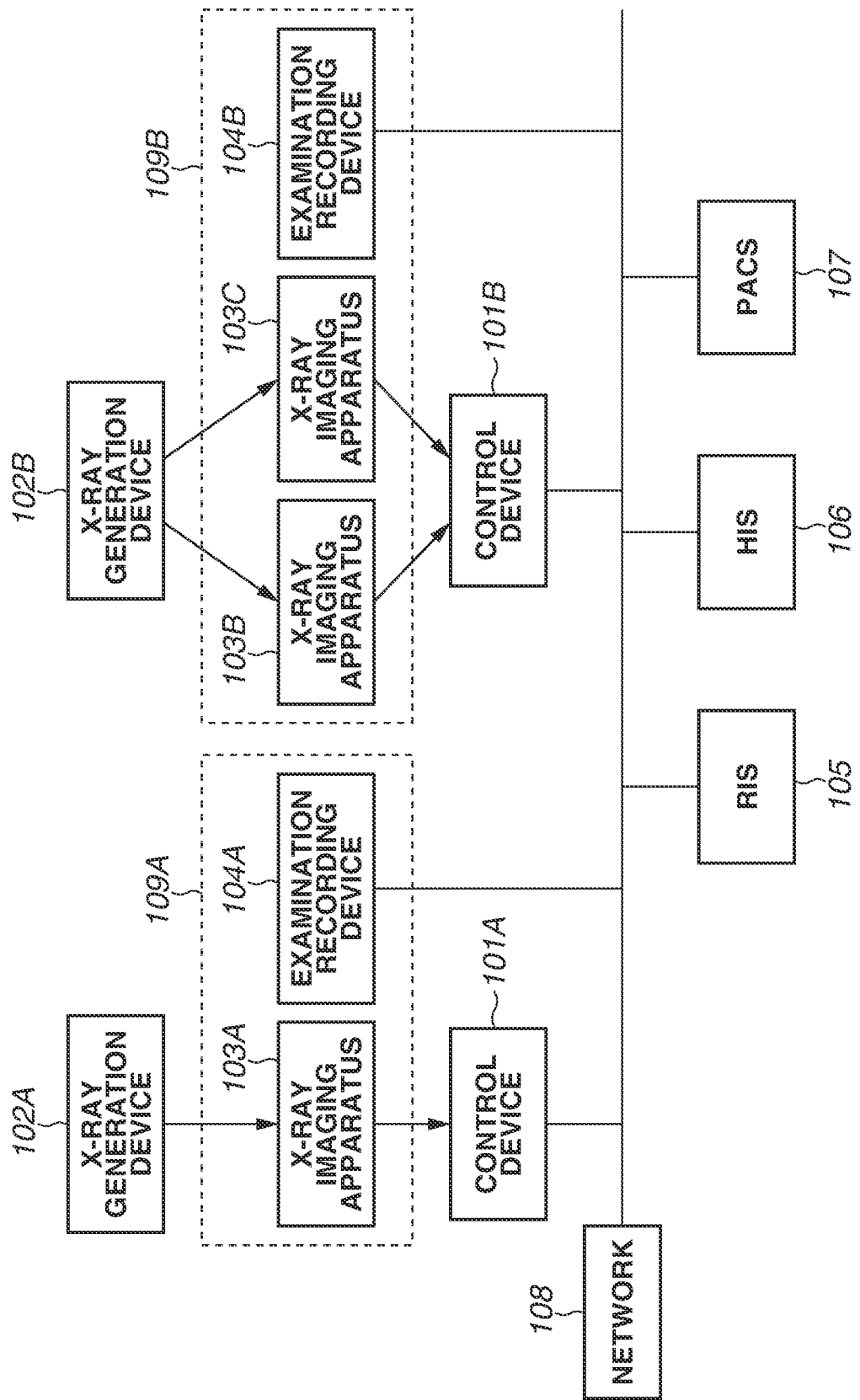
FIG. 1 illustrates an example of a configuration of a radiographing system according to a first exemplary embodiment.

FIG. 1 illustrates an example of a configuration of a radiographing system (hereinafter referred to as an "X-ray imaging system") according to a first exemplary embodiment.

As illustrated in FIG. 1, the X-ray imaging system includes, for example, control devices 101A and 101B, X-ray generation devices 102A and 102B, X-ray imaging apparatuses (radiographing apparatuses) 103A, 103B, and 103C, examination recording devices (mobile terminals) 104A and 104B, a radiology information system (RIS) 105, a hospital information system (HIS) 106, and a picture archiving and communication system (PACS) (image server) 107. Moreover, the control devices 101A and 101B, the examination recording devices 104A and 104B, the RIS 105, the HIS 106, and the PACS 107 are electrically interconnected via a network 108, which is configured with, for example, a local area network (LAN) or a wide area network (WAN).

The control devices 101A and 101B have the same function and are able to individually discriminate a subject. Hereinafter, in a case where the control devices 101A and 101B do not need to be individually distinguished, those are referred to as a "control device 101A, 101B." Similarly, in a case where the X-ray generation devices 102A and 102B, the X-ray imaging apparatuses (radiographing apparatuses) 103A to 103C, and the examination recording devices 104A and 104B do not need to be individually distinguished, those are referred to as an "X-ray generation device 102A, 102B," an "X-ray imaging apparatus 103A, 103B, 103C," and an "examination recording device 104A, 104B," respectively.

The control device 101A, 101B performs image management, such as image processing of an X-ray image (radiation image) and image outputting to the PACS 107, and performs information management about, for example, an examination order and an examination progress situation in cooperation with the RIS 105 or the HIS 106. Moreover, the control device 101A, 101B communicates with the X-ray imaging apparatus 103A, 103B, 103C and the examination recording device 104A, 104B by wired or wireless connection, and performs association using an X-ray image acquired from the X-ray imaging apparatus 103A, 103B, 103C and an examination time included in examination-related information acquired from the examination recording device 104A, 104B.

The examination recording device (mobile terminal) 104A, 104B stores an examination time of a subject that is based on examination-related information about the subject. The X-ray imaging apparatus (radiographing apparatus) 103A, 103B, 103C takes a radiation image of the subject, and stores an imaging time of the radiation image. Then, the control device 101A, 101B functions as an association unit to associate the X-ray image (radiation image) with the examination-related information based on the imaging time of the X-ray image (radiation image) and the examination time.

The examination-related information includes at least one of examination information and examination implementation information. The examination information includes at least one of the subject name, the subject identifier (ID), the date of birth, the gender, the examination ID, the date and time of examination, the examination location, and the radiographic procedure about a subject. The examination implementation information includes at least one of the implementation sequence of the radiographic procedure, failed radiography information about an X-ray image (radiation image), and the amount of radiation used for the X-ray imaging apparatus (radiographing apparatus) 103A, 103B, 103C.

In the present exemplary embodiment, the examination-related information includes examination information (for example, the name of patient, the patient ID, the date of birth, the gender, the examination ID, the date and time of examination, the patients' room, and the radiographic procedure) and examination implementation information (for example, the implementation sequence of the radiographic procedure, failed radiography information, and the amount of radiation).

The X-ray generation device 102A, 102B irradiates a subject and the X-ray imaging apparatus 103A, 103B, 103C with X-rays. Examples of the X-ray generation device 102A, 102B include a device of the type that is fixed at a radiographic room and a device of the type that is movable to an optional location for rounds or in case of disaster.

The X-ray imaging apparatus 103A, 103B, 103C function as a detector configured to detect X-rays that have passed through the subject to acquire an X-ray image that is based on the subject, thus taking an X-ray image (radiation image) of the subject. The X-ray imaging apparatus 103A, 103B, 103C is electrically connectable to the examination recording device (mobile terminal) 104A, 104B, which stores examination-related information about the subject, and takes an X-ray image (radiation image) of the subject based on the examination-related information.

The examination recording device 104A, 104B is a mobile terminal (for example, a portable mobile terminal, such as a mobile phone and a smart device) that is electrically connectable to the X-ray imaging apparatus (radiographing apparatus) 103A, 103B, 103C, and manages examination-related information. The examination information, which is a piece of information included in the examination-related information, can be directly input to the examination recording device 104A, 104B by the operation of an operator, or can be generated by the examination recording device 104A, 104B based on the examination order acquired from the RIS 105 or the HIS 106 via the network 108. The examination recording device 104A, 104B enables the operator to confirm a patient to be radiographed (a subject) and a radiographic procedure.

Furthermore, the examination recording device 104A, 104B receives an input from the operator and stores examination implementation information, such as examination implementation time, such as start time and end time of an examination (an examination time), the presence or absence of failed radiography, and the amount of radiation acquired from the X-ray generation device 102A, 102B. The examination implementation information, which is a piece of information included in the examination-related information, can be directly input to the examination recording device 104A, 104B by the operation of the operator, or can be generated by the examination recording device 104A, 104B based on the examination order acquired from the RIS 105 or the HIS 106 via the network 108.

Furthermore, the configuration illustrated in FIG. 1 is merely an example, and can be changed in constituent element or number of elements as appropriate. For example, while the control device 101A, 101B illustrated in FIG. 1 is connected to various devices via the network 108, the control device 101A, 101B does not necessarily need to be connected to such devices.

Figure 2:
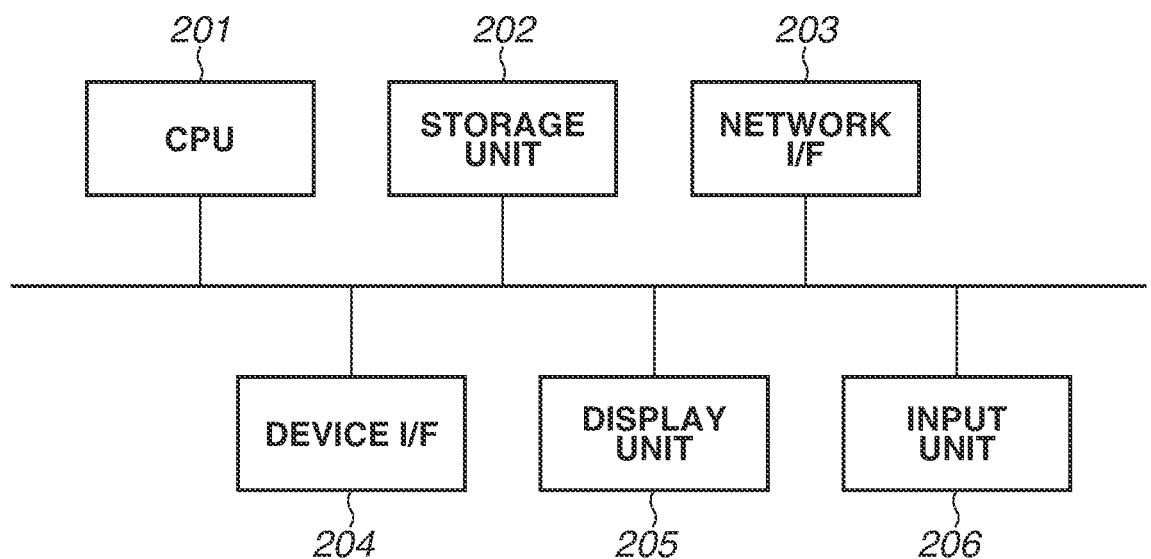
FIG. 2 is a block diagram illustrating an example of a control device in the radiographing system.

Next, details of the respective apparatuses or devices are described. FIG. 2 is a block diagram illustrating an example of the control device 101A, 10B in the X-ray imaging system (radiographing system). The control device 101A, 101B includes a central processing unit (CPU) 201, a storage unit 202, a network interface (I/F) 203, a device I/F 204, a display unit 205, and an input unit 206.

The CPU 201 comprehensively controls the entire control device 101A, 101B. The storage unit 202 stores, for example, image data, various programs, and examination-related information. The network I/F 203 functions as an input-output unit by electrically connecting to the network 108 and communicating with another apparatus or device. The device I/F 204 electrically connects to the X-ray imaging apparatus 103A, 103B, 103C and functions as an input-output unit.

The display unit 205 is, for example, a liquid crystal display and displays various pieces of information, such as an image and examination-related information, to the operator. The input unit 206 includes, for example, a mouse and a keyboard, and inputs various instructions and various pieces of information from the operator to the control device 101A, 101B. The display unit 205 and the input unit 206 can be integrated into a touch panel.

Figure 3:
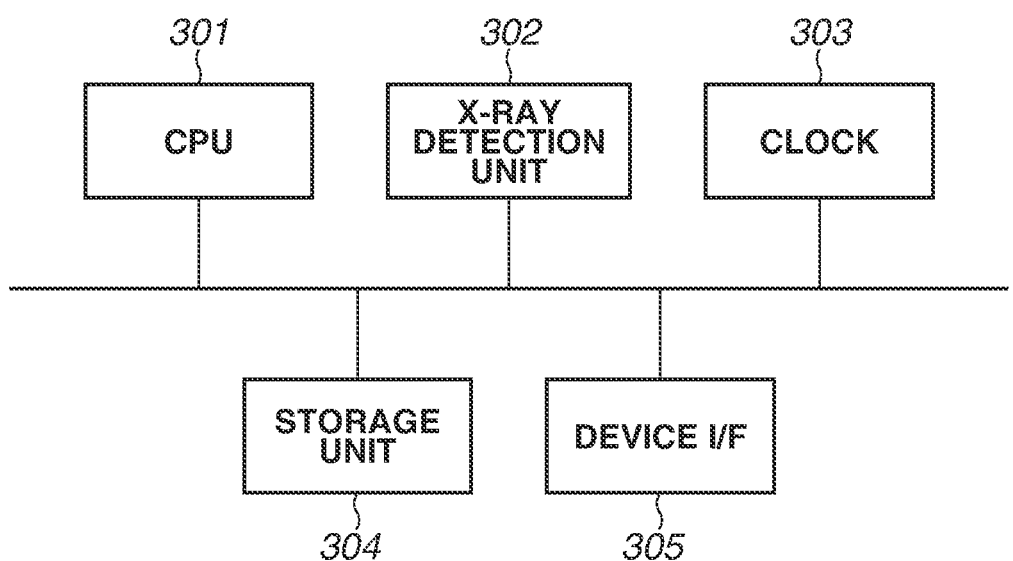
FIG. 3 is a block diagram illustrating an example of a radiographing apparatus.

FIG. 3 is a block diagram illustrating an example of the X-ray imaging apparatus (radiographing apparatus) 103A, 103B, 103C in the X-ray imaging system. The X-ray imaging apparatus 103A, 103B, 103C includes a CPU 301, an X-ray detection unit 302, a clock 303, a storage unit 304, and a device I/F 305.

The CPU 301 controls the entire X-ray imaging apparatus 103A, 103B, 103C. X-rays detected by the X-ray detection unit 302 are converted into an image, and the image is stored in the storage unit 304. The clock 303 is used to acquire imaging time (a radiographing time) of an X-ray image. The imaging time is stored in the storage unit 304 in association with the X-ray image. The storage unit 304 has a capacity sufficient to store examination-related information, a plurality of X-ray images, and their imaging times. The device I/F 305 electrically connects to the control device 101A, 101B and the examination recording device 104A, 104B, and functions as an input-output unit to transmit an X-ray image (radiation image) and imaging time of the X-ray image and to receive examination-related information (including examination implementation time).

Figure 4:
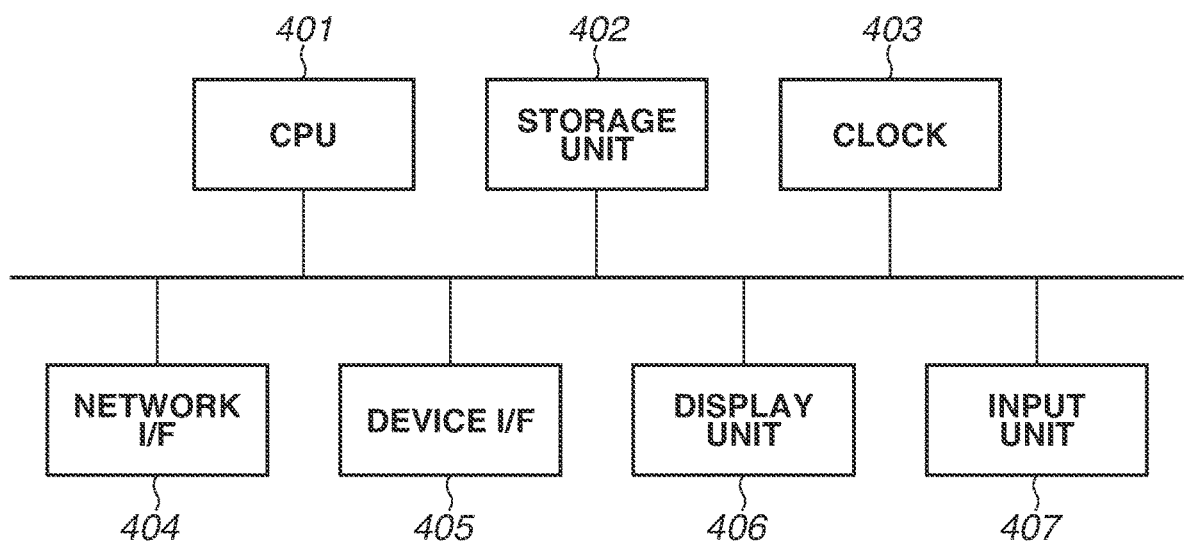
FIG. 4 is a block diagram illustrating an example of a mobile terminal.

FIG. 4 is a block diagram illustrating an example of the examination recording device (mobile terminal) 104A, 104B in the X-ray imaging system. The examination recording device 104A, 104B includes a CPU 401, a storage unit 402, a clock 403, a network I/F 404, a device I/F 405, a display unit 406, and an input unit 407.

The CPU 401 comprehensively controls the entire examination recording device 104A, 104B. The storage unit 402 stores, for example, a control program and examination-related information. The clock 403 is used to acquire examination implementation time (an examination time). The examination implementation time is stored in the storage unit 402 in association with the examination-related information. The storage unit 402 stores examination implementation time (an examination time) of a subject based on examination-related information about the subject.

The network I/F 404 connects to the network 108, and function as an input-output unit by communicating with another apparatus or device. The device I/F 405 is able to communicate with the X-ray imaging apparatus 103A, 103B, 103C and the X-ray generation device 102A, 102B, and functions as an input-output unit.

The display unit 406 is, for example, a liquid crystal display and displays an X-ray image (radiation image) and various pieces of information, such as examination-related information, to the operator. The input unit 407 includes, for example, a mouse, operation buttons, and an optical camera, and functions as an input unit to input various instructions and various pieces of information from the operator to the examination recording device 104A, 104B. The display unit 406 and the input unit 407 can be integrated into a touch panel.

Here, in the X-ray imaging system illustrated in FIG. 1, processing for associating an X-ray image with examination-related information is described based on the flow of examination. The examination recording device (mobile terminal) 104A, 104B is grouped with one or more X-ray imaging apparatuses 103A, 103B, 103C. Then, the control device (association unit) 101A, 101B associates an X-ray image (radiation image) obtained by an X-ray imaging apparatus 103A, 103B, 103C grouped with an examination recording device 104A, 104B with examination-related information stored in the examination recording device (mobile terminal) 104A, 104B.

Figure 5:
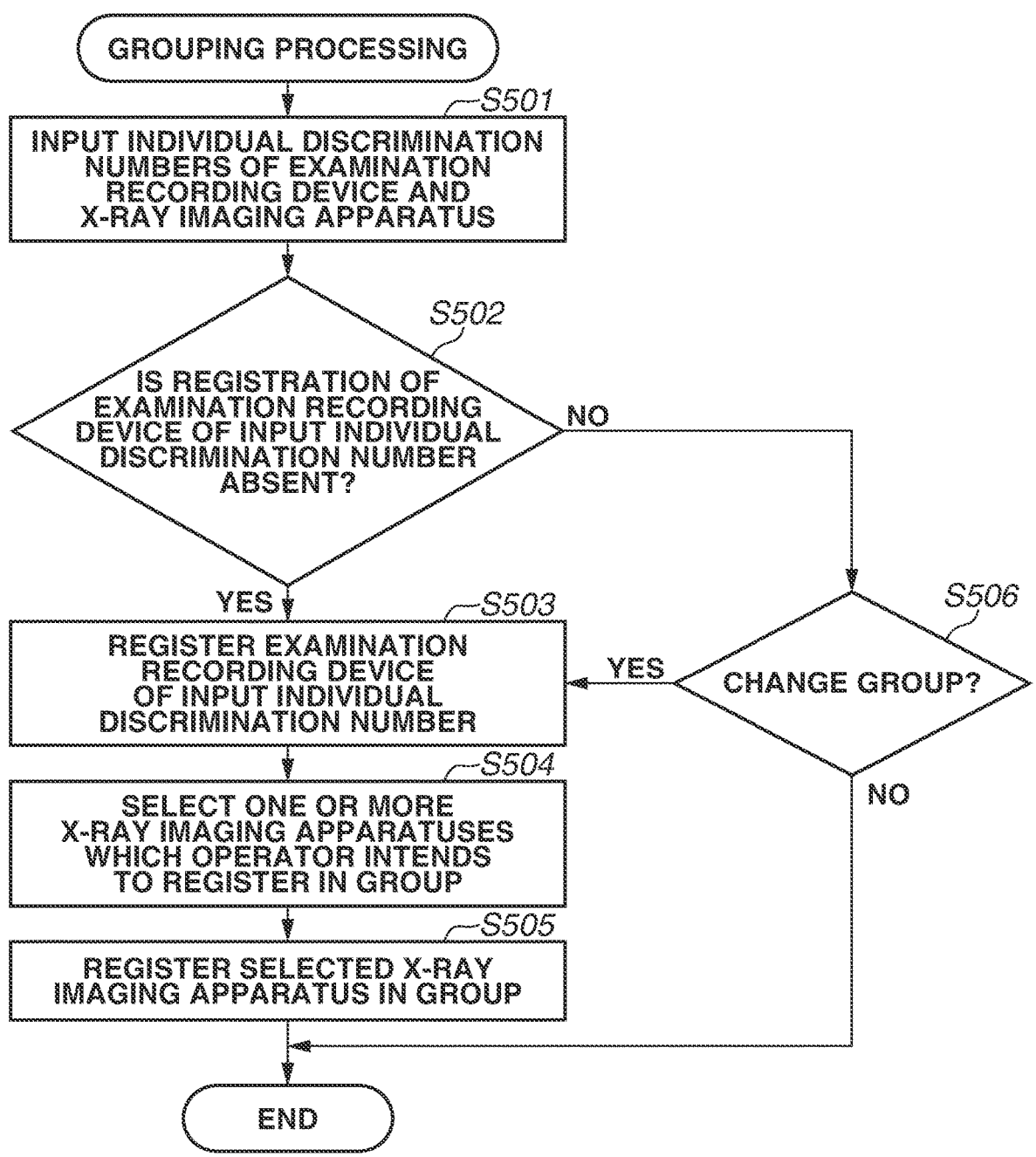
FIG. 5 is a flowchart illustrating an example of processing for grouping the mobile terminal and the radiographing apparatus.
Figure 6:
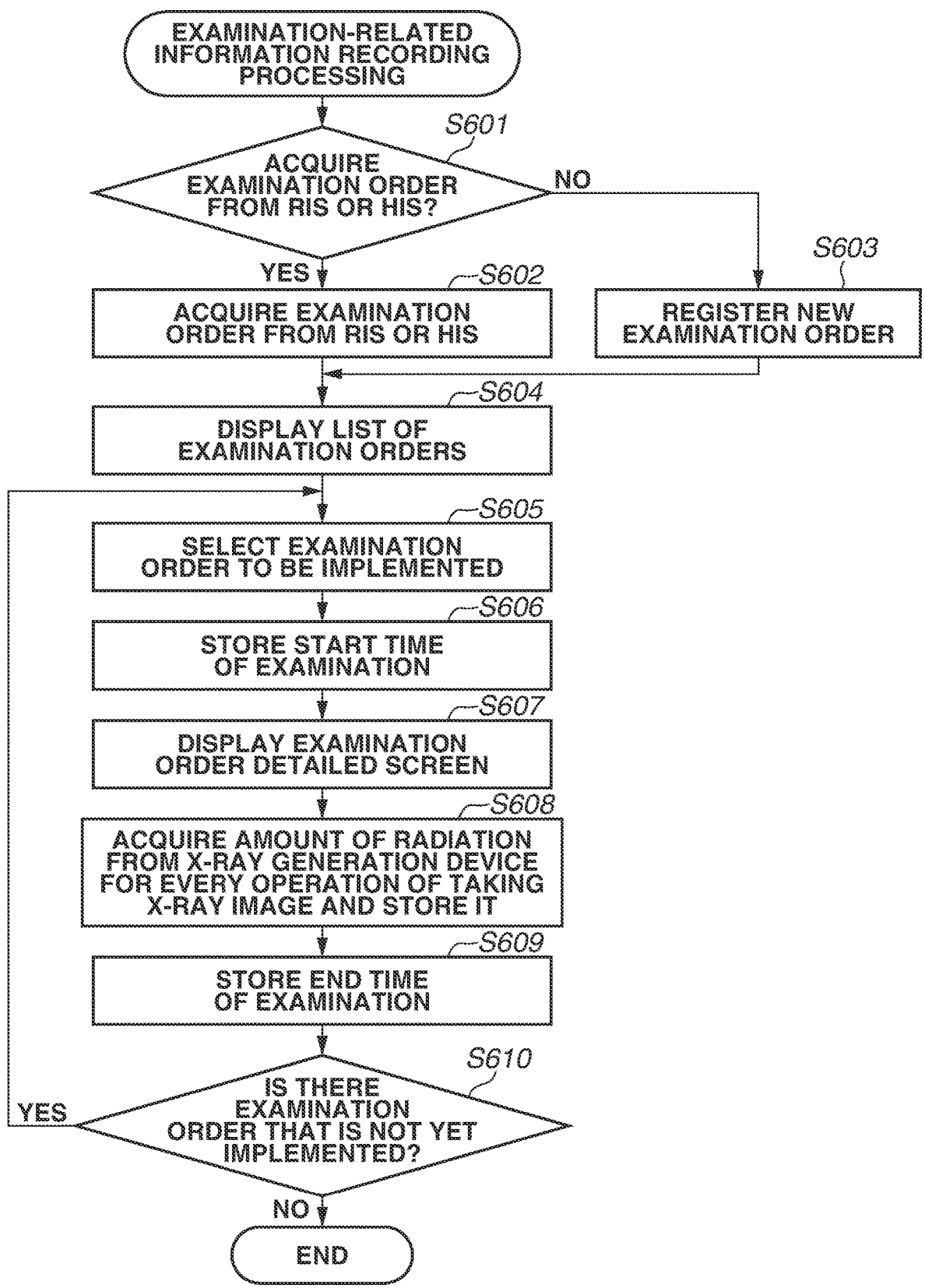
FIG. 6 is a flowchart illustrating an example of processing for recording examination-related information, which is performed by the mobile terminal, according to the first exemplary embodiment.

FIG. 5 is a flowchart illustrating an example of grouping processing for the examination recording device (mobile terminal) 104A, 104B and the X-ray imaging apparatus (radiographing apparatus) 103A, 103B, 103C. FIG. 6 is a flowchart illustrating an example of examination-related information recording processing performed by the examination recording device (mobile terminal) 104A, 104B.

First, as examination preparation processing, the control device 101A, 101B performs grouping processing for the examination recording device (mobile terminal) 104A, 104B and the X-ray imaging apparatus (radiographing apparatus) 103A, 103B, 103C. The grouping processing is processing for uniquely associating the examination recording device 104A, 104B and the X-ray imaging apparatus 103A, 103B, 103C with each other. One group is configured with one examination recording device 104A, 104B and one or more X-ray imaging apparatuses 103A, 103B, 103C.

While a plurality of groups is able to be registered, an examination recording device 104A, 104B and an X-ray imaging apparatus 103A, 103B, 103C are not allowed to be concurrently registered in a plurality of groups. For example, the examination recording device 104A registered in the group 109A is not allowed to be concurrently registered in the group 109B. Each group can be dissolved or altered by the operation of the operator.

As illustrated in FIG. 5, in step S501, the operator inputs the individual discrimination numbers of the examination recording device 104A, 104B and the X-ray imaging apparatus 103A, 103B, 103C to the control device 101A, 101B. The individual discrimination numbers can be input via, for example, a keyboard, or can be input by reading barcodes attached to the examination recording device 104A, 104B and the X-ray imaging apparatus 103A, 103B, 103C. Alternatively, with the examination recording device 104A, 104B and the X-ray imaging apparatus 103 connected to the control device 101A, 101B, the individual discrimination numbers can be transmitted from the examination recording device 104A, 104B and the X-ray imaging apparatus 103A, 103B, 103C to the control device 101A, 101B and then input to the control device 101A, 101B.

If it is determined that the registration of the examination recording device 104A, 104B of the input individual discrimination number is absent (not registered in any group) (YES in step S502), then in step S503, the control device 101A, 101B generates a new group and registers the examination recording device 104A, 104B.

For example, the control device 101A, 101B causes the display unit 205 to display apparatuses that are not registered in any group from among the X-ray imaging apparatuses 103A, 103B, 103C the individual discrimination numbers of which have previously been input. When, in step S504, the operator selects one or more X-ray imaging apparatuses 103A, 103B, 103C which the operator intends to register, then in step S505, the control device 101A, 101B registers the selected X-ray imaging apparatus 103A, 103B, 103C in the group generated in step S503.

At this time, in a case where a plurality of control devices 101A, 101B is able to communicate with each other, registration information about each group can be shared between the plurality of control devices 101A, 101B. Furthermore, the grouping processing can be performed by the examination recording device 104A, 104B. In this case, the individual discrimination number of the X-ray imaging apparatus 103A, 103B, 103C to be used for examination can be previously registered with the examination recording device 104A, 104B and, when the examination recording device 104A, 104B is connected to the control device 101A, 101B, registration information about the group can be transmitted to the control device 101A, 101B.

If it is determined that the registration of the examination recording device 104A, 104B of the input individual discrimination number is not absent (registered in a group) (NO in step S502), then in step S506, the control device 101A, 101B determines whether to change the group of the examination recording device 104A, 104B.

In the case of changing the group of the examination recording device 104A, 104B (YES in step S506), then in step S503, the control device 101A, 101B changes the group of the examination recording device 104A, 104B and registers the changed group. In the case of not changing the group of the examination recording device 104A, 104B (NO in step S506), the grouping processing ends.

Next, recording processing of examination-related information is described. As illustrated in FIG. 6, in step S601, the operator selects, via the selection screen of the examination recording device 104A, 104B, whether to acquire the examination order from the RIS 105 or the HIS 106.

In the case of acquiring the examination order from the RIS 105 or the HIS 106 (YES in step S601), then in step S602, the examination order is acquired from the RIS 105 or the HIS 106. For example, in a case where a button for generating examination information based on the examination order acquired from the RIS 105 is pressed in the selection screen of the examination recording device 104A, 104B (YES in step S601), the examination recording device 104A, 104B causes the display unit 406 to display a search screen illustrated in FIG. 7.

The operator inputs a search condition for examination information which the operator intends to acquire (at least one of the patient name, the patient ID, the date of birth, the gender, the examination ID, the date and time of examination, and the patients' room) to a search condition input portion 701. After entry of the search condition, in response to the press of an examination acquisition button 702, the examination recording device 104A, 104B transmits an examination acquisition request including the search condition input to the search condition input portion 701 to the RIS 105 via the network 108. In step S602, the RIS 105, which has received the examination acquisition request, transmits an examination order that matches the search condition to the examination recording device 104A, 104B.

In the case of not acquiring the examination order from the RIS 105 or the HIS 106 (NO in step S601), then in step S603, a new examination order is registered according to the input operation of the operator. In a radiographing system that does not use the RIS 105 or the HIS 106, step S601 is omitted, so that a new examination order can be registered according to the input operation of the operator.

Figure 8:
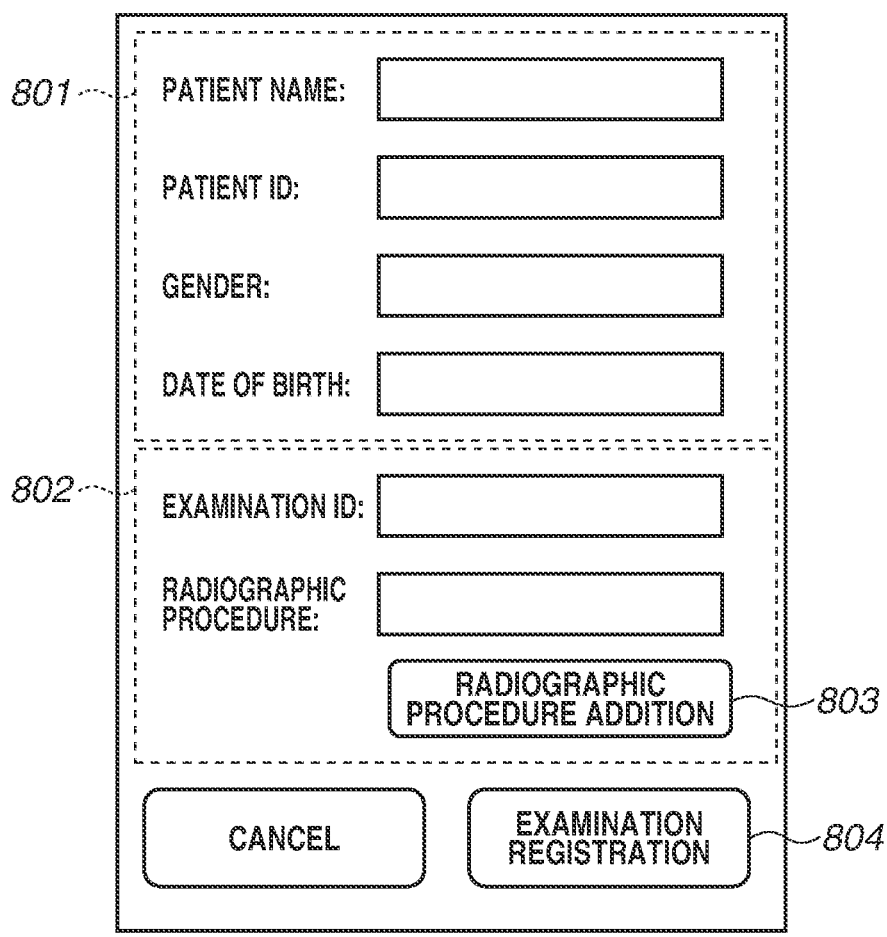
FIG. 8 illustrates an example of a new examination registration screen, which is displayed by the display unit.

For example, in a case where a button for registering a new examination order based on information input by the operator is pressed in the selection screen of the examination recording device 104A, 104B (NO in step S601), the examination recording device 104A, 104B causes the display unit 406 to display a new examination registration screen illustrated in FIG. 8.

The new examination registration screen includes a patient information input portion 801, an examination information input portion 802, a procedure addition button 803, and an examination registration button 804. The operator inputs examination information about a patient (for example, the patient name, the patient ID, the gender, and the date of birth) to the patient information input portion 801, and inputs examination information about an examination (for example, the examination ID and the radiographic procedure) to the examination information input portion 802. Here, the examination information about a patient can be input by reading, for example, a barcode attached to the patient with, for example, an optical camera or a barcode reader.

Pressing the procedure addition button 803 enables registering a plurality of radiographic procedures. In step S603, after entry of the examination information, in response to the press of the examination registration button 804, a new examination order is registered.

Figure 9:
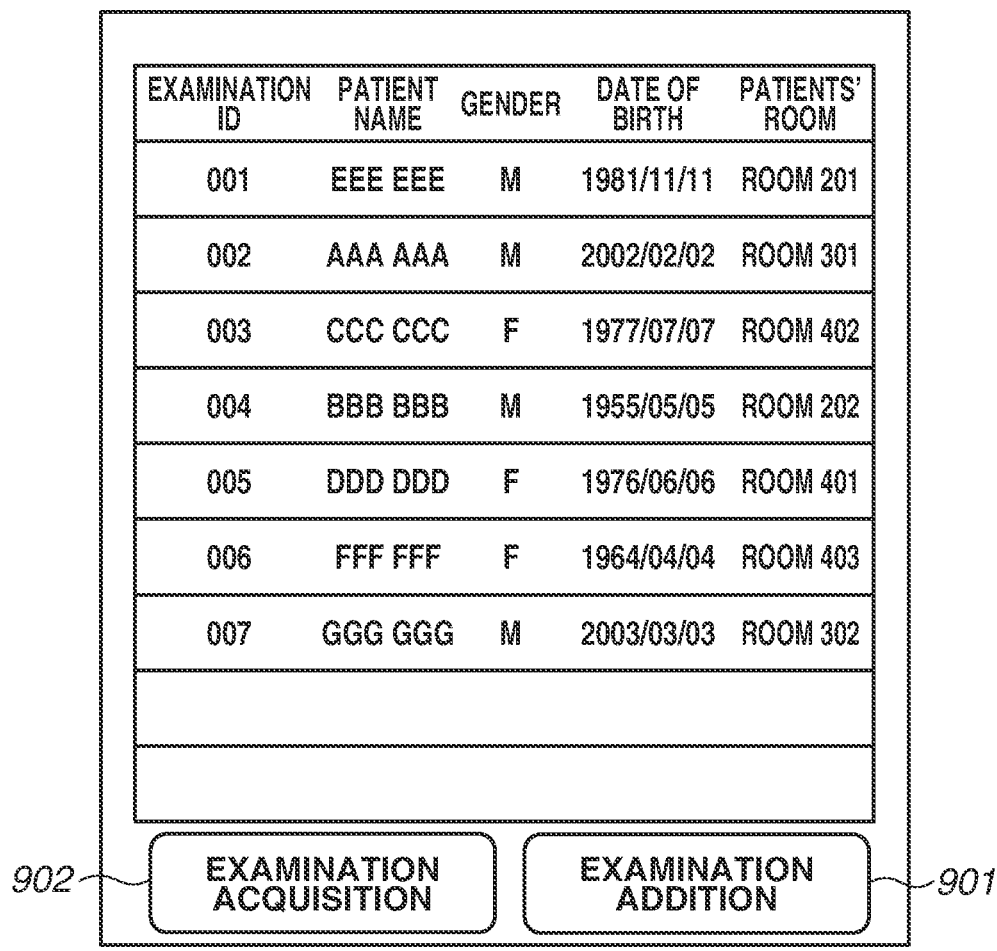
FIG. 9 illustrates an example of an examination information list screen in which examination information is displayed.

FIG. 9 illustrates an example of an examination information list screen in which the examination information is displayed. In step S604, examination information generated based on the examination order acquired from the RIS 105 or examination information generated based on the new registered examination order is displayed in the examination information list screen of the examination recording device 104A, 104B as illustrated in FIG. 9. Both the examination information generated based on the examination order acquired from the RIS 105 and the examination information generated based on the new registered examination order can be displayed in the examination information list screen.

In response to the press of an examination addition button 901, the new examination registration screen illustrated in FIG. 8 is displayed by the examination recording device 104A, 104B, so that examination information can be added. Furthermore, in response to the press of an examination acquisition button 902, the search screen illustrated in FIG. 7 is displayed by the examination recording device 104A, 104B, so that a further examination order can be acquired and examination information can be generated.

In step S605, the operator confirms examination information about the patient via the examination information list screen, and selects an examination order to be implemented (examination implementation information) from the list. In response to the selection of examination implementation information, in step S606, the examination recording device 104A, 104B acquires the current time of the clock 303 as the start time of examination, and stores the start time of examination in the storage unit 402 in association with the examination-related information. In this way, the examination recording device (mobile terminal) 104A, 104B stores, as the start time, the time at which examination-related information about the subject was selected.

Figure 10:
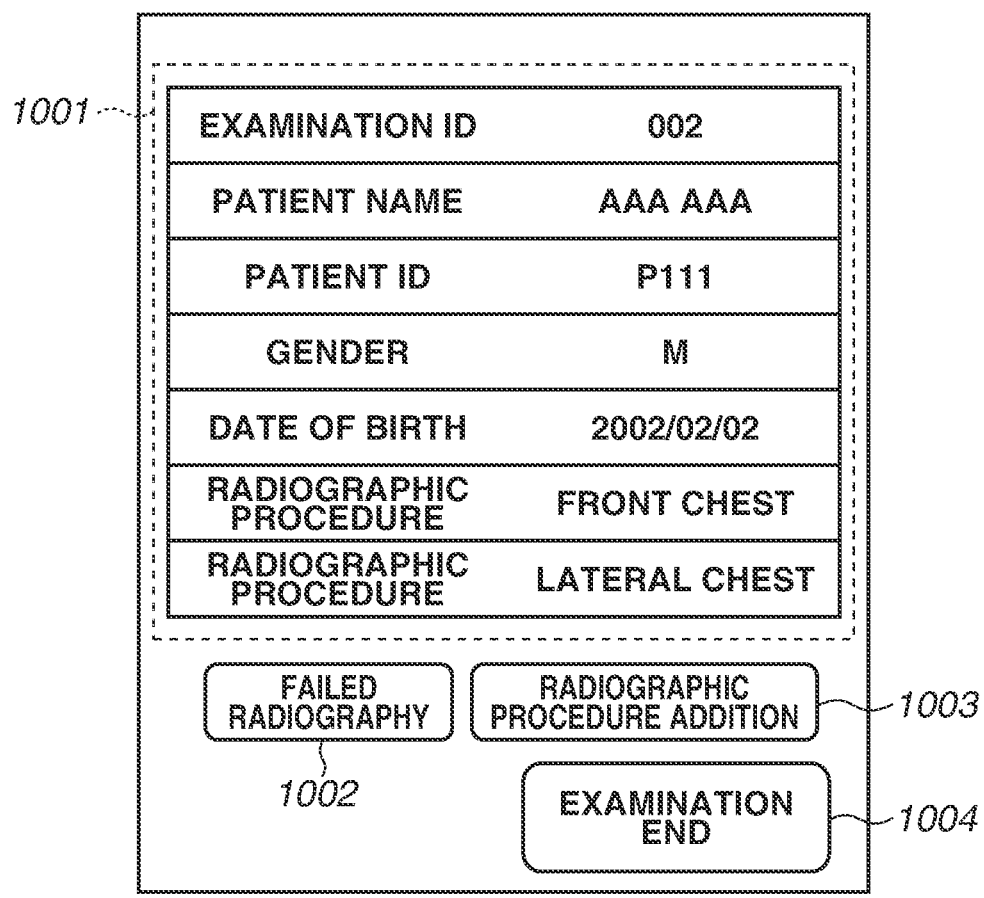
FIG. 10 illustrates an example of an examination order detailed screen, which is displayed by the display unit.

In step S607, the examination recording device 104A, 104B causes the display unit 406 to display an examination order detailed screen illustrated in FIG. 10. The examination order detailed screen includes a detailed information display portion 1001, a failed radiography button 1002, a procedure addition button 1003, and an examination end button 1004. Examination information, such as the examination ID, the patient name, patient ID, the gender, the date of birth, the radiographic procedure, and the patients' room, is displayed in the detailed information display portion 1001.

Since an operation for selecting examination-related information about a patient and displaying examination information such as the radiographic procedure serves also as an operation for recording the start time, the operator does not need to consciously perform recording of the start time. Furthermore, since it is usually unlikely that the operator performs radiography without confirming examination information such as the radiographic procedure, it is possible to reduce the risk that the start time is not recorded.

In a case where a failed radiography of an X-ray image (radiation image) described below has occurred, the operator selects a radiographic procedure performed at the time of occurrence of the failed radiography and presses the failed radiography button 1002. In response to the press of the failed radiography button 1002, the examination recording device 104A, 104B stores failed radiography information indicating the occurrence of a failed radiography as examination implementation information in the storage unit 402 in association with the radiographic procedure, and duplicates a similar radiographic procedure in the examination information detailed screen.

Figure 11:
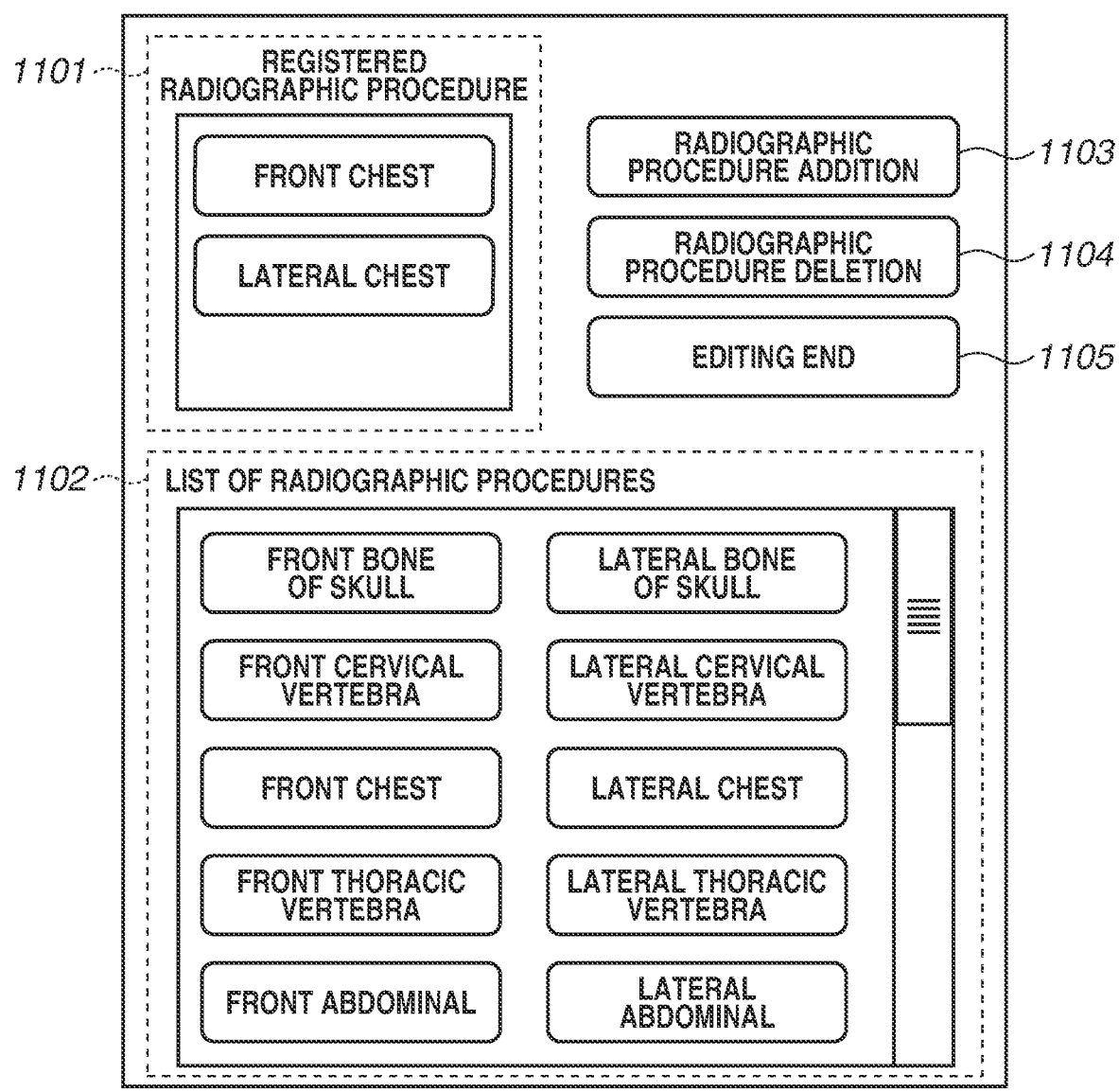
FIG. 11 illustrates an example of a procedure editing screen, which is displayed by the display unit.

In the case of adding a radiographic procedure that is not registered due to a factor of, for example, the patient (subject) or radiography environment, the procedure addition button 1003 is pressed. In response to the press of the procedure addition button 1003, a procedure editing screen illustrated in FIG. 11 is displayed. The procedure editing screen includes a registered procedure button 1101, a procedure list display portion 1102, a procedure addition button 1103, a procedure deletion button 1104, and an editing end button 1105.

When a radiographic procedure is selected from the procedure list display portion 1102 and the procedure addition button 1103 is pressed, the radiographic procedure can be added. Furthermore, when a radiographic procedure is selected from the registered procedure button 1101 and the procedure deletion button 1104 is pressed, the radiographic procedure can be deleted. The addition and deletion of a radiographic procedure can be performed by, for example, an operation such as drag and drop, instead of a button operation.

The operator confirms a radiographic procedure displayed in the detailed information display portion 1001, and performs setting of radiography and positioning of a patient. When a series of radiographing preparation operations is completed, the operator operates and causes the X-ray generation device 102A, 102B to radiate X-rays toward a subject (for example, a specific site of the patient), and causes the X-ray imaging apparatus 103A, 103B, 103C to detect X-rays that have passed through the subject. This results in taking of an X-ray image (radiation image).

In step S608, the examination recording device 104A, 104B acquires the amount of radiation of X-rays from the X-ray generation device 102A, 102B as examination implementation information at the time of every operation of taking an X-ray image, and stores the amount of radiation in the storage unit 402 in the order of acquisition. The acquisition of the amount of radiation can be performed by an input operation of the operator.

When these processes are iterated, imaging operations for all of the radiographic procedures displayed in the detailed information display portion 1001 are performed. When all of the imaging operations are completed, the operator presses the examination end button 1004. This completes a series of examination operations, and, in step S609, the examination recording device 104A, 104B acquires the current time of the clock 403 as the end time of examination, and stores the end time of examination in the storage unit 402 in association with the examination-related information.

In response to the press of the examination end button 1004, the examination recording device 104A, 104B re-displays the examination information list screen illustrated in FIG. 9. In this way, the examination recording device (mobile terminal) 104A, 104B stores, as the end time, the time at which the examination-related information about the subject was displayed.

In step S610, the operator checks whether there is an examination order that is not yet implemented in the examination information list screen. If there is an examination order that is not yet implemented (YES in step S610), the examination recording device 104A, 104B selects a next examination order from the re-displayed examination information list screen.

Since an operation for displaying the examination information list screen (examination-related information) serves also as an operation for recording the end time, the operator does not need to consciously perform recording of the end time. Furthermore, since, to select the next examination order, it is necessary to press the examination end button 1004 and display the examination information list screen, it is possible to reduce the risk that the end time is not recorded.

If taking for all of the pieces of examination information to be implemented is completed (NO in step S610), the operator electrically connects the X-ray imaging apparatus 103A, 103B, 103C and the examination recording device 104A, 104B to the control device 101A, 101B. In a case where registration information about groups is shared between a plurality of control devices 101A, 101B, the X-ray imaging apparatus 103A, 103B, 103C and the examination recording device 104A, 104B can be connected to an optional control device 101A, 101B that shares the registration information about groups.

For example, when the control device 101A registers the group 109A, the X-ray imaging apparatus 103A and the examination recording device 104A which belong to the group 109A can be connected to the control device 101B, which shares registration information about the group 109A. Furthermore, even in a case where the examination recording device 104A, 104B stores registration information about groups, the X-ray imaging apparatus 103A, 103B, 103C and the examination recording device 104A, 104B can be connected to an optional control device 101A, 101B.

When all of the apparatuses or devices registered in a group enter a state of being able to communicate with the control device 101A, 101B, the control device 101A, 101B starts receiving data. Furthermore, when the operator operates the control device 101A, 101B and presses a data reception start button, the control device 101A, 101B can start receiving data.

An X-ray image and its imaging time are transmitted from the X-ray imaging apparatus 103A, 103B, 103C to the control device 101A, 101B via the device I/F 204. Implemented examination-related information and its start time and end time are transmitted from the examination recording device 104A, 104B to the control device 101A, 101B via the network 108. Upon completion of reception of data, the control device (association unit) 101A, 101B stores the received data in the storage unit 202, and performs processing for associating the examination-related information and the X-ray image (radiation image).

The control device (association unit) 101A, 101B inputs at least one of the start time and end time of an examination of the subject associated by the examination recording device (mobile terminal) 104A, 104B and the examination-related information. Then, the control device (association unit) 101A, 101B associates at least one of an X-ray image (radiation image) taken from the start time and an X-ray image (radiation image) taken until the end time with the examination-related information (for example, the subject name and the examination ID). In the processing for associating the X-ray image (radiation image) and the examination-related information, X-ray images taken between the start time and end time included in each piece of examination-related information and their imaging times are extracted from the storage unit 202, and each extracted X-ray image is associated with corresponding examination-related information.

While, in the present exemplary embodiment, the start time and end time of an examination are used, the control device (association unit) 101A, 101B can extract X-ray images taken during the time from the start time of a predetermined examination to the start time of a next examination and associate the X-ray images with the corresponding pieces of examination-related information. Furthermore, the control device (association unit) 101A, 101B can extract X-ray images taken during the time from the end time of a predetermined examination to the end time of a next examination and associate the X-ray images with the corresponding pieces of examination-related information.

According to the present exemplary embodiment, a radiation image is automatically associated with examination-related information about a subject, so that radiography can be made more efficient while the risk for patient mix-up and any other misunderstandings is decreased.

The control device (association unit) 101A, 101B can associate an X-ray image (radiation image) with examination-related information based on an imaging sequence of the X-ray image (radiation image) and an implementation sequence of an examination included in the examination-related information. For example, after associating X-ray images (radiation images) with examination-related information, the control device 101A,101B serially associates an X-ray image (radiation image) the imaging time of which is earlier with examination-related information which is earlier in examination sequence among pieces of examination-related information based on at least one of the start time and end time.

The control device 101A, 101B is able to associate an X-ray image (radiation image) with examination-related information based on an imaging time of the X-ray image (radiation image) and an examination time included in the examination-related information and the imaging sequence of the X-ray image (radiation image) and the implementation sequence included in the examination-related information. In other words, even in the case of performing a plurality of radiographing operations on one and the same subject, the control device 101A, 101B is able to associate an X-ray image (radiation image) with examination-related information.

The control device (association unit) 101A, 101B associates at least one of an X-ray image (radiation image) taken from the start time and an X-ray image (radiation image) taken until the end time with examination-related information based on the imaging sequence of the X-ray image (radiation image) and the acquisition sequence of examination-related information. With this, if at least one of the start time and end time is found, matching is performed between the imaging sequence and the examination sequence based on the found time, so that an X-ray image (radiation image) and examination-related information can be associated with each other.

Furthermore, the control device (association unit) 101A, 101B is also able to associate at least one of an X-ray image (radiation image) taken from the start time and an X-ray image (radiation image) taken until the end time with the amount of radiation based on the imaging sequence of the X-ray image (radiation image) and the acquisition sequence of the amount of radiation.

When the processing for associating an X-ray image (radiation image) with examination-related information is completed for all of the pieces of examination-related information, the control device 101A, 101B ends a series of examination operations, and outputs or stores X-ray images (radiation images) and corresponding pieces of examination-related information in the associated state. For example, X-ray images (radiation images) and corresponding pieces of examination-related information are output to or stored in, for example, the PACS 107, the RIS 105, the storage unit 202, and a printer (not illustrated). At this time, examination-related information with which no X-ray image (radiation image) is associated is treated as being unimplemented.

According to the present exemplary embodiment, a radiation image is automatically associated with examination-related information, so that radiography can be made more efficient while the risk for patient mix-up and any other misunderstandings is decreased.

Next, a second exemplary embodiment is described. In the second exemplary embodiment, the examination recording device 104A, 104B further records the implementation sequence of a radiographic procedure as examination implementation information, and associates an X-ray image (radiation image) with a radiographic procedure. Furthermore, the configuration, function, and operation similar to those of the above-described exemplary embodiment are omitted from description, and differences between the above-described exemplary embodiment and the present exemplary embodiment are mainly described.

Figure 12:
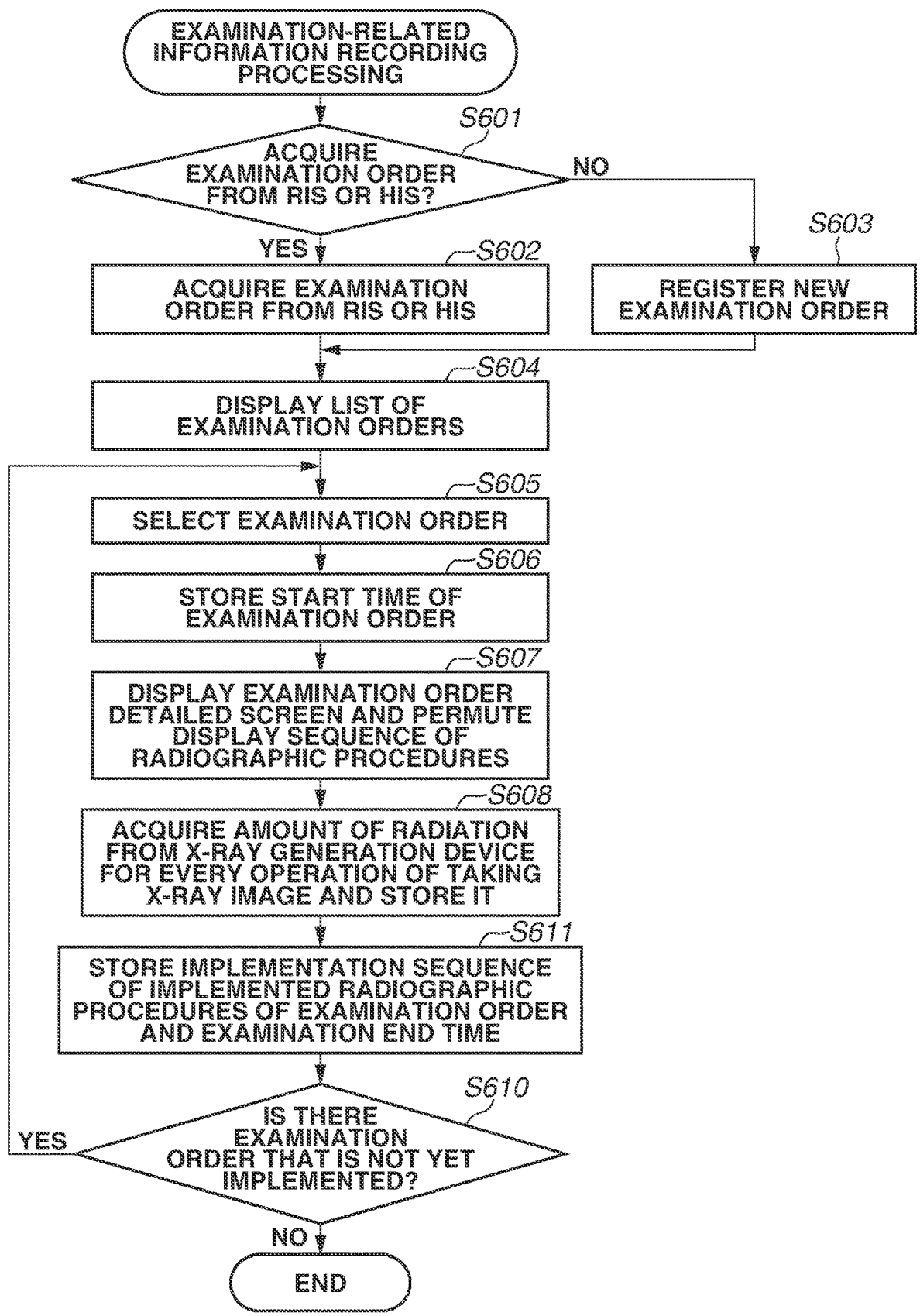
FIG. 12 is a flowchart illustrating an example of processing for recording examination-related information, which is performed by the mobile terminal, according to a second exemplary embodiment.

First, as in the first exemplary embodiment, the grouping processing illustrated in FIG. 5 is performed. Next, examination-related information recording processing is performed. FIG. 12 is a flowchart illustrating an example of examination-related information recording processing performed by the examination recording device (mobile terminal) 104A, 104B.

When radiography is performed while the radiographic procedure is confirmed in step S607, radiography may not be performed in the sequence of radiographic procedures displayed in the detailed information display portion 1001 illustrated in FIG. 10 due to a factor, such as the patient (subject), the imaging efficiency, and the imaging environment. In a case where the display sequence and the implementation sequence of radiographic procedures are different from each other as mentioned above, the operator permutes the display sequence of radiographic procedures in the detailed information display portion 1001 in conformity with the implementation sequence. In a case where radiography is performed exactly in the sequence of radiographic procedures displayed in the detailed information display portion 1001, the operator does not need to permute the display sequence of radiographic procedures in the detailed information display portion 1001.

When all of the imaging operations, the recording operations for the amount of radiation, and the permutation of radiographic procedures are completed, the operator presses the examination end button 1004. In response to the press of the examination end button 1004, in step S611, the examination recording device 104A, 104B stores the implementation sequence of radiographic procedures as examination implementation information in the storage unit 402. Then, the examination recording device 104A, 104B acquires the current time of the clock 403 as the examination end time, and stores the examination end time in the storage unit 402 in association with the examination-related information.

While, in the present exemplary embodiment, the implementation sequence is recorded with the displayed radiographic procedures permuted, for example, a numerical entry field can be provided near (for example, lateral to) the radiographic procedure field and the implementation sequence of radiographic procedures can be recorded by a method of, for example, inputting the implementation sequence into the numerical entry field.

If taking for all of the pieces of examination information to be implemented is completed (NO in step S610), as in the above-described exemplary embodiment, the X-ray imaging apparatus 103A, 103B, 103C and the examination recording device 104A, 104B are electrically connected to the control device 101A, 101B, thus transmitting data to the control device 101A, 101B. In the present exemplary embodiment, data about radiographic procedures and the implementation sequence of the radiographic procedures is transmitted from the examination recording device 104A, 104B to the control device 101A, 101B via the network 108.

Upon completion of reception of data, the control device (association unit) 101A, 101B associates an X-ray image (radiation image) with examination-related information (for example, the subject name and the examination ID) based on the imaging sequence of the X-ray image (radiation image) and the implementation sequence of an examination included in the examination-related information, as in the above-described exemplary embodiment.

After associating X-ray images (radiation images) with examination-related information, the control device 101A, 101B serially associates an X-ray image (radiation image) the imaging time of which is earlier with examination-related information which is earlier in examination sequence among pieces of examination-related information based on at least one of the start time and end time. The examination recording device (mobile terminal) 104A, 104B stores a radiographic procedure for taking an X-ray image (radiation image). Then, the control device (association unit) 101A, 101B associates at least one of an X-ray image (radiation image) taken from the start time and an X-ray image (radiation image) taken until the end time with a radiographic procedure based on the imaging sequence of the X-ray image and the implementation sequence of radiographic procedures.

When the processing for associating an X-ray image (radiation image) with examination-related information is completed for all of the pieces of examination-related information, the control device 101A, 101B ends a series of examination operations, and outputs or stores X-ray images (radiation images) and corresponding pieces of examination-related information in the associated state. For example, X-ray images (radiation images) and corresponding pieces of examination-related information are output to or stored in, for example, the PACS 107, the RIS 105, the storage unit 202, and a printer (not illustrated).

At this time, examination-related information or a radiographic procedure with which no X-ray image (radiation image) is associated is treated as being unimplemented. Furthermore, an X-ray image (radiation image) corresponding to the radiographic procedure with which failed radiography information is associated is treated as being a failed radiography image, and the failed radiography image is output to, for example, a PACS 107 exclusively used for failed radiography images.

According to the present exemplary embodiment, a radiation image is automatically associated with a radiographic procedure, so that radiography can be made more efficient while the risk for patient mix-up and any other misunderstandings is decreased.

Next, a third exemplary embodiment is described. In the third exemplary embodiment, after the association processing, a result of association is displayed, and the operator is allowed to edit the association. Furthermore, the configuration, function, and operation similar to those of the above-described exemplary embodiments are omitted from description, and differences between the above-described exemplary embodiments and the present exemplary embodiment are mainly described.

After performing the association processing according to the above-described first exemplary embodiment or second exemplary embodiment, the control device 101A, 101B causes the display unit 205 to display an association result screen illustrated in FIG. 13. The association result screen includes an examination time display portion 1301, an examination information display portion 1302, a thumbnail display portion 1303, an imaging time display portion 1304, a procedure addition button 1306, an examination addition button 1307, and an association confirmation button 1308.

In a case where the number of pieces of examination-related information and the number of X-ray images (radiation images) are large, a scroll bar 1305 is displayed, and the operator is allowed to scroll using the scroll bar 1305 to display examination-related information and an X-ray image (radiation image) corresponding to an optional time region.

The examination time display portion 1301 is used to display the start time or end time in each piece of examination-related information. The examination information display portion 1302 is used to display examination information (for example, the examination ID, the patient name, the patient ID, the date of birth, the gender, and the radiographic procedure) and examination implementation information (for example, the amount of radiation and failed radiography information) in each piece of examination-related information, and a starting point 1310 or ending point 1311 of each examination is also displayed.

A radiographic procedure 1309 which is associated with an X-ray image (radiation image) is, for example, displayed at the location corresponding to the same time as that of a thumbnail of the X-ray image (radiation image) in the thumbnail display portion 1303, so that the relationship between the radiographic procedure and the X-ray image (radiation image) is explicitly indicated. Furthermore, with regard to failed radiography information, the failed radiography information is displayed in examination information or a color or mark is attached to the radiographic procedure, so that the occurrence of failed radiography is explicitly indicated.

Each piece of examination-related information can be selected and more detailed examination-related information can be displayed. The thumbnail display portion 1303 is used to display a thumbnail of each X-ray image. A thumbnail can be selected and an enlarged X-ray image can be displayed to increase the visibility of the X-ray image. Furthermore, the thumbnail display portion 1303 can be also used to display the content of examination-related information associated with the current X-ray image. The imaging time display portion 1304 is used to display the imaging time of each X-ray image.

The operator checks for the association result screen to determine whether there is an X-ray image (radiation image) associated with examination-related information (for example, a radiographic procedure) that differs from the actual one or an X-ray image (radiation image) associated with no examination-related information.

For example, in a case where radiography for a next examination is performed without the examination recording device 104A, 104B completing an examination or in a case where a next examination is started before completion of radiography, examination-related information that differs from the actual one and an X-ray image (radiation image) are associated with each other. Furthermore, in a case where radiography is performed without the examination recording device 104A, 104B starting an examination, an X-ray image (radiation image) that is not associated with any examination-related information is generated.

In these cases, the operator drags and drops a thumbnail of the X-ray image (radiation image) to examination-related information with which the operator intends to associate the X-ray image, so that the X-ray image is associated with the actual examination-related information (for example, the actual radiographic procedure). With this, the examination-related information (for example, the radiographic procedure) is changed and associated with the X-ray image (radiation image).

Furthermore, in a case where taking of an X-ray image (radiation image) is performed before the examination recording device 104A, 104B inputs examination-related information for the reason that an examination is urgently performed and there is no examination-related information associated with the X-ray image, the operator presses the examination addition button 1307. In response to the press of the examination addition button 1307, an examination addition screen illustrated in FIG. 14 is displayed by the display unit 205.

The examination addition screen includes a patient information input portion 1401, a procedure list display portion 1402, a selected procedure deletion button, and an examination addition button 1404. For example, the patient name and the date of birth are input to the patient information input portion 1401, and a radiographic procedure is selected from the procedure list display portion 1402. Then, when the examination addition button 1404 is pressed, examination-related information is generated based on the input information, and the generated examination-related information is associated with an X-ray image (radiation image).

In a case where the examination recording device 104A, 104B is not operated to add a procedure regardless of the fact that radiography is performed with a radiographic procedure that is not registered in examination information due to a factor of, for example, the patient or the radiography environment, X-ray images the number of which exceeds the number of procedures registered in examination information are associated with examination-related information. As a result, an X-ray image with which there is no radiographic procedure to be associated is generated.

In this case, the control device 101A, 101B displays an X-ray image that is not associated with any radiographic procedure and a list of radiographic procedures registered in the storage unit 202. When the operator selects a radiographic procedure to be associated with the X-ray image, the control device 101A, 101B adds the selected radiographic procedure to examination information to be associated with the X-ray image. In this way, in a case where the number of X-ray images (radiation image) exceeds the number of radiographic procedures, the control device (association unit) 101A, 101B inputs a radiographic procedure and associates an X-ray image (radiation image), which lacks association, with the input radiographic procedure.

After completing editing of the association, the operator presses the association confirmation button 1308. In a case where an X-ray image (radiation image) that is not associated with any radiographic procedure remains, the control device 101A, 101B prompts the operator to input a radiographic procedure and associate the radiographic procedure with an X-ray image (radiation image), and causes the display unit 205 to display an X-ray image (radiation image) that is not associated with any radiographic procedure.

In a case where all of the X-ray images are associated with corresponding radiographic procedures, in response to the press of the association confirmation button 1308, a series of examination operations ends. The control device 101A, 101B confirms the association between X-ray images (radiation images) and examination-related information, and outputs or stores the X-ray images (radiation images) and examination-related information to or in, for example, the PACS 107, the RIS 105, the storage unit 202, and a printer (not illustrated).

At this time, examination-related information (for example, a radiographic procedure) with which no X-ray image is associated is treated as being unimplemented. In other words, in a case where the number of radiographic procedures exceeds the number of X-ray images (radiation images), the control device (association unit) 101A, 101B records a radiographic procedure that is not associated with any X-ray image (radiation image) as an unimplemented radiographic procedure. Furthermore, an X-ray image (radiation image) corresponding to the radiographic procedure with which failed radiography information is associated is treated as being a failed radiography image, and the failed radiography image is output to, for example, a PACS 107 exclusively used for failed radiography images.

Next, a fourth exemplary embodiment is described. In the fourth exemplary embodiment, association processing is performed by the examination recording device (mobile terminal) 104A, 104B. In this case, the examination recording device 104A, 104B is a mobile terminal that is electrically connectable to the X-ray imaging apparatus (radiographing apparatus) 103A, 103B, 103C, which takes an X-ray image (radiation image) of a subject and stores an imaging time of the X-ray image (radiation image).

Furthermore, the storage unit 402 of the examination recording device (mobile terminal) 104A, 104B stores an examination time of a subject based on examination-related information about the subject. Then, the CPU (association unit) 401 of the examination recording device (mobile terminal) 104A, 104B associates an X-ray image (radiation image) with examination-related information (for example, the subject name, the examination ID, the amount of radiation, and the radiographic procedure) based on the imaging time and the examination time.

The following is a detailed description. First, the examination recording device 104A, 104B performs grouping processing. The individual discrimination number of the X-ray imaging apparatus 103A, 103B, 103C used for examination is registered with the examination recording device 104A, 104B.

Next, the examination-related information recording processing illustrated in FIG. 6 is performed as in the above-described exemplary embodiment. When all of the imaging operations are completed, the examination recording device 104A, 104B and the X-ray imaging apparatus 103A, 103B, 103C are electrically connected to each other via the device I/F 305 and the device I/F 405. In a case where the connected X-ray imaging apparatus 103A, 103B, 103C is previously registered in a group, the examination recording device 104A, 104B starts receiving data when becoming able to communicate with the X-ray imaging apparatus 103A, 103B, 103C. Furthermore, when the operator operates the examination recording device 104A, 104B and presses the data reception start button, the examination recording device 104A, 104B can start receiving data.

An X-ray image and its imaging time are transmitted from the X-ray imaging apparatus 103A, 103B, 103C to the examination recording device 104A, 104B. Upon completion of reception of the data, the CPU (association unit) 401 of the examination recording device 104A, 104B stores the received data in the storage unit 402 and performs association processing for the X-ray image (radiation image) and examination-related information.

In a case where radiography is performed by a plurality of X-ray imaging apparatuses 103A, 103B, 103C included in the same group, the examination recording device 104A, 104B receives an X-ray image and its imaging time from each X-ray imaging apparatus 103A, 103B, 103C. While the examination recording device 104A, 104B receives X-ray images and their imaging times from all of the X-ray imaging apparatuses 103A, 103B, 103C registered in a group, association processing is started by the operator operating the examination recording device 104A, 104B and pressing the association processing start button.

Processing for associating examination-related information and an X-ray image (radiation image) is performed in the same method as that in the above-described exemplary embodiment. For example, the storage unit 402 of the examination recording device 104A, 104B stores at least one of the start time and end time of an examination of a subject in association with examination-related information. The CPU (association unit) 401 of the examination recording device 104A, 104B associates at least one of an X-ray image (radiation image) taken from the start time and an X-ray image (radiation image) taken until the end time with the examination-related information.

When the processing for associating examination-related information and an X-ray image is completed, the examination recording device 104A, 104B ends a series of examination operations, and outputs or stores X-ray images (radiation images) and corresponding pieces of examination-related information in the associated state. For example, X-ray images (radiation images) and corresponding pieces of examination-related information are output to or stored in, for example, the PACS 107, the RIS 105, the storage unit 402, and a printer (not illustrated). At this time, examination-related information with which no X-ray image (radiation image) is associated is treated as being unimplemented. After the association processing, the examination recording device 104A, 104B can be used to display a result of association and to allow the operator to edit the association as in the above-described exemplary embodiment.

According to the present exemplary embodiment, connecting the examination recording device 104A, 104B to the X-ray imaging apparatus 103A, 103B, 103C enables associating a radiation image with examination-related information, so that radiography can be made more efficient while the risk for patient mix-up and any other misunderstandings is decreased.

Next, a fifth exemplary embodiment is described. In the fifth exemplary embodiment, association processing is performed by the X-ray imaging apparatus (radiographing apparatus) 103A, 103B, 103C. In this case, the X-ray imaging apparatus 103A, 103B, 103C is a radiographing apparatus that is electrically connectable to the examination recording device (mobile terminal) 104A, 104B, which stores examination-related information about a subject, and that takes an X-ray image (radiation image) of a subject based on examination-related information and stores an imaging time of the X-ray image.

Furthermore, the CPU (association unit) 301 of the X-ray imaging apparatus 103A, 103B, 103C inputs an examination time of a subject from the examination recording device (mobile terminal) 104A, 104B, and associates an X-ray image with examination-related information (for example, the subject name, the examination ID, the amount of radiation, and the radiographic procedure) based on the imaging time and the examination time.

The following is a detailed description. First, grouping processing and examination-related information recording processing are performed as in the above-described exemplary embodiment.

When all of the imaging operations are completed, the examination recording device 104A, 104B and the X-ray imaging apparatus 103A, 103B, 103C are electrically connected to each other via the device I/F 305 and the device I/F 405. In a case where the connected X-ray imaging apparatus 103A, 103B, 103C is previously registered in a group, the examination recording device 104A, 104B starts transmitting data when becoming able to communicate with the X-ray imaging apparatus 103A, 103B, 103C. Furthermore, when the operator operates the examination recording device 104A, 104B and presses the data transmission start button, the examination recording device 104A, 104B can start transmitting data.

The implemented examination-related information and its start time and end time are transmitted from the examination recording device 104A, 104B to the X-ray imaging apparatus 103A, 103B, 103C. Upon completion of reception of data, the X-ray imaging apparatus 103A, 103B, 103C stores the received data in the storage unit 304, and performs processing for associating examination-related information and an X-ray image (radiation image).

In a case where radiography is performed by a plurality of X-ray imaging apparatuses 103A, 103B, 103C included in the same group, the examination recording device 104A, 104B is connected to each X-ray imaging apparatus 103A, 103B, 103C and transmits the implemented examination-related information and its start time and end time to each X-ray imaging apparatus 103A, 103B, 103C.

Processing for associating examination-related information and an X-ray image (radiation image) is performed in the same method as that in the above-described exemplary embodiment. For example, the CPU (association unit) 301 of the X-ray imaging apparatus (radiographing apparatus) 103A, 103B, 103C inputs at least one of the start time and end time of the examination of a subject associated by the examination recording device 104A, 104B and the examination-related information. Then, the CPU (association unit) 301 associates at least one of an X-ray image (radiation image) taken from the start time and an X-ray image (radiation image) taken until the end time with the examination-related information.

When the processing for associating examination-related information and an X-ray image is completed, the X-ray imaging apparatus 103A, 103B, 103C outputs or stores the X-ray image (radiation image) and the examination-related information in the associated state to or in, for example, the control device 101A, 101B and the storage unit 304. At this time, examination-related information with which no X-ray image (radiation image) is associated is deleted.

Furthermore, the X-ray imaging apparatus 103A, 103B, 103C can be provided with a network I/F and can output the X-ray image (radiation image) and the examination-related information in the associated state to, for example, the PACS 107, the RIS 105, and a printer (not illustrated). Moreover, the X-ray imaging apparatus 103A, 103B, 103C can be provided with a display unit and an input unit, and, after the association processing, the X-ray imaging apparatus 103A, 103B, 103C can be used to display a result of association and to allow the operator to edit the association as in the above-described exemplary embodiment.

According to the present exemplary embodiment, connecting the X-ray imaging apparatus 103A, 103B, 103C to the examination recording device 104A, 104B enables associating a radiation image with examination-related information, so that radiography can be made more efficient while the risk for patient mix-up and any other misunderstandings is decreased.

While the present disclosure has been described above with reference to exemplary embodiments, the invention is not limited to the disclosed exemplary embodiments, but can be altered or modified within the scope set forth in the claims.

The present disclosure can be embodied by supplying software (program) that implements functions of the above-described exemplary embodiments to a system or apparatus via a network or various storage media and causing a computer (CPU or micro processing unit (MPU)) of the system or apparatus to read out and execute the program. Moreover, the present disclosure can also be implemented by processing for causing at least one processor of the computer of the system or apparatus to read out and execute the program, or can also be implemented by a circuit that implements at least one function (for example, an application specific integrated circuit (ASIC)).

OTHER EMBODIMENTS

Embodiments of the present disclosure can also be realized by a computer of a system or apparatus that reads out and executes computer executable instructions recorded on a storage medium (e.g., non-transitory computer-readable storage medium) to perform the functions of one or more of the above-described embodiment(s), and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random access memory (RAM), a read-only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-074473 filed Apr. 1, 2016, which is hereby incorporated by reference herein in its entirety.

What is claimed is:

1. A radiographing system comprising:
at least one mobile terminal configured to store an examination time that is based on examination-related information about a subject;
at least one radiographing apparatus configured to take at least one radiation image of the subject and to store an imaging time of the at least one radiation image; and
an association unit configured to associate the at least one radiation image with the examination-related information based on the imaging time and the examination time.

2. The radiographing system according to claim 1,
wherein the association unit inputs at least one of a start time and an end time of an examination of the subject associated by the at least one mobile terminal and the examination-related information, and
associates at least one of: a) a radiation image of the at least one radiation image taken from the start time and b) a radiation image of the at least one radiation image taken at the end time, with the examination-related information.

3. The radiographing system according to claim 2, wherein the association unit associates the at least one radiation image of the subject with the examination-related information based on an imaging sequence of the at least one radiation image and an implementation sequence of an examination included in the examination-related information.

4. The radiographing system according to claim 2, wherein the at least one mobile terminal stores an amount of radiation used for taking the at least one radiation image of the subject, and wherein the association unit associates at least one of: a) the radiation image taken from the start time and b) the radiation image taken at the end time, with the amount of radiation based on an imaging sequence of the at least one radiation image of the subject and an acquisition sequence of the amount of radiation.

5. The radiographing system according to claim 2, wherein the at least one mobile terminal stores at least one radiographic procedure used for taking the at least one radiation image of the subject, and wherein the association unit associates at least one of: a) the radiation image taken from the start time and h) the radiation image taken at the end time, with the at least one radiographic procedure based on an imaging sequence of the at least one radiation image of the subject and an implementation sequence of the at least one radiographic procedure.

6. The radiographing system according to claim 5, wherein the at least one radiation image comprises a plurality of radiation images, wherein the at least one radiographic procedure comprises a plurality of radiographic procedures, and wherein, in a case where a number of the plurality of radiation images exceeds a number of the plurality of radiographic procedures, the association unit inputs a radiographic procedure of the plurality of radiographic procedures and associates the at least one radiation image of the plurality of radiation images, which lacks association, with the input radiographic procedure.

7. The radiographing system according to claim 5,
wherein the at least one radiation image comprises a plurality of radiation images,
wherein the at least one radiographic procedure comprises a plurality of radiographic procedures, and
wherein, in a case where a number of the plurality of radiographic procedures exceeds a number of the plurality of radiation images, the association unit records a radiographic procedure of the plurality of radiographic procedures, which is not associated with a radiation image of the plurality of radiation images, as an unimplemented radiographic procedure.

8. The radiographing system according to claim 2, wherein the at least one mobile terminal stores a time at which the examination-related information is selected or displayed as the start time or the end time.

9. The radiographing system according to claim 1,
wherein the examination-related information includes at least one of examination information and examination implementation information,
wherein the examination information includes at least one member selected from the group consisting of a subject name of the subject, a subject identifier (ID) of the subject, a date of birth of the subject, a gender of the subject, an examination ID, an examination date and time, an examination location, and a radiographic procedure, and
wherein the examination implementation information includes at least one member selected from the group consisting of an implementation sequence of the radiographic procedure, failed radiography information about the at least one radiation image, and an amount of radiation used for the at least one radiographing apparatus.

10. The radiographing system according to claim 1, wherein the at least one radiographing apparatus comprises a plurality of radiographing apparatuses,
wherein the at least one mobile terminal is grouped with at least one of the plurality of radiographing apparatuses, and
wherein the association unit associates the at least one radiation image, which is obtained by the at least one of the plurality of radiographing apparatuses grouped with the at least one mobile terminal, with the examination-related information stored in the at least one mobile terminal.

11. A mobile terminal for electrically connecting to a radiographing apparatus that takes a radiation image of a subject and stores an imaging time of the radiation image, the mobile terminal comprising:
a storage unit configured to store an examination time of the subject that is based on examination-related information about the subject; and
an association unit configured to associate the radiation image with the examination-related information based on the imaging time and the examination time.

12. The mobile terminal according to claim 11,
wherein the storage unit stores at least one of a start time and an end time of an examination of the subject in association with the examination-related information, and
wherein the association unit associates at least one of: a) a radiation image taken from the start time and b) a radiation image taken at the end time, with the examination-related information.

13. A radiographing apparatus for electrically connecting to a mobile terminal which stores examination-related information about a subject, and takes a radiation image of the subject based on the examination-related information and stores an imaging time of the radiation image, the radiographing apparatus comprising:
an association unit configured to input an examination time of the subject from the mobile terminal and to associate the radiation image with the examination-related information based on the imaging time and the examination time.

14. The radiographing apparatus according to claim 13, wherein the association unit inputs at least one of a start time and an end time of an examination of the subject associated by the mobile terminal and the examination-related information, and
associates at least one of: a) a radiation image taken from the start time and b) a radiation image taken at the end time, with the examination-related information.

15. A radiographing method comprising:
storing an examination time of a subject that is based on examination-related information about the subject;
taking a radiation image of the subject and storing an imaging time of the radiation image; and
associating the radiation image with the examination-related information based on the imaging time and the examination time.

16. A non-transitory computer-readable storage medium storing computer-executable instructions that, when executed by a computer, cause the computer to perform a radiographing method comprising:
storing an examination time of a subject that is based on examination-related information about the subject;
taking a radiation image of the subject based on the examination-related information and storing an imaging time of the radiation image; and
associating the radiation image with the examination-related information based on the imaging time and the examination time.

* * * * *